US010350129B2

(12) United States Patent
Takenaka et al.

(10) Patent No.: US 10,350,129 B2
(45) Date of Patent: Jul. 16, 2019

(54) WALKING ASSIST DEVICE

(71) Applicant: HONDA MOTOR CO., LTD., Tokyo (JP)

(72) Inventors: Toru Takenaka, Wako (JP); Tatsuya Ishikawa, Wako (JP); Ken Yasuhara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 632 days.

(21) Appl. No.: 15/155,603

(22) Filed: May 16, 2016

(65) Prior Publication Data

US 2016/0338897 A1 Nov. 24, 2016

(30) Foreign Application Priority Data

May 19, 2015 (JP) ................................ 2015-101892

(51) Int. Cl.

| | |
|---|---|
| ***A61F 3/00*** | (2006.01) |
| ***A61H 3/00*** | (2006.01) |
| ***A61H 1/02*** | (2006.01) |

(52) U.S. Cl.

CPC ............ *A61H 3/00* (2013.01); *A61H 1/0244* (2013.01); *A61H 2003/007* (2013.01); *A61H 2201/1215* (2013.01); *A61H 2201/164* (2013.01); *A61H 2201/165* (2013.01); *A61H 2201/1628* (2013.01); *A61H 2201/5007* (2013.01); *A61H 2201/5058* (2013.01)

(58) Field of Classification Search

CPC ........... A61H 3/00; A61F 5/0102; A61F 2/60

See application file for complete search history.

(56) References Cited

U.S. PATENT DOCUMENTS

| | | | | |
|---|---|---|---|---|
| 2011/0033835 A1* | 2/2011 | Endo | G09B 19/0038 | 434/365 |
| 2016/0022440 A1* | 1/2016 | Ha | A61F 2/68 | 623/24 |
| 2016/0101515 A1* | 4/2016 | Lim | A61H 3/00 | 623/24 |
| 2016/0151227 A1* | 6/2016 | Choi | A61H 3/00 | 623/27 |

FOREIGN PATENT DOCUMENTS

| | | |
|---|---|---|
| WO | 2009084387 A1 | 9/2009 |
| WO | 2013094747 A1 | 6/2013 |

* cited by examiner

*Primary Examiner* — Jason-Dennis N Stewart

(74) *Attorney, Agent, or Firm* — Armstrong Teasdale LLP

(57) ABSTRACT

Provided is a walking assist device including a main frame configured to be worn by a user, a power unit mounted on the main frame, a pair of power transmission members for transmitting assist force provided by the power unit to femoral parts of the user and a control unit for controlling an operation of the power unit, wherein the control unit comprises a differential angle computation unit for computing a differential angle between angular positions of the femoral parts of the user about respective hip joints of the user; a differential angle phase computation unit for computing a differential angle phase according to the differential angle; and an assist force computation unit for computing an assist force to be applied to the user according to the differential angle phase.

9 Claims, 17 Drawing Sheets

WALKING ASSIST DEVICE

TECHNICAL FIELD

The present invention relates to a walking assist device for assisting a walking movement of a user.

BACKGROUND ART

In recent years, various forms of motion assist devices configured to be worn by a user for medical and nursing purposes have been developed. As a control principle for such motion assist devices, a timing matching control for matching the timings of the user and the device is known. See Patent Document 1. According to the concept of the timing matching control, it is expected that the motion assist device is enabled to operate with a timing that favorably matches the timing of the walking movement of the user or is enabled to operate as a rehabilitation device with a motion teaching function by providing an assist force that teaches an optimum motion to the user before the user actually effects a corresponding motion. In the motion assist device of Patent Document 1, a mutually inhibiting model of a neural oscillator is used for generating a movement pattern of synchronization.

According to a motion assist device proposed in Patent Document 2, the motion assist device uses a phase oscillator model using the phase of the motion of the user as an input oscillation of the phase oscillator, and operates by causing a freely selected phase difference with respect of the motion of the user.

PRIOR ART DOCUMENT(S)

Patent Document(s)

Patent Document 1: WO2009/084387 A1
Patent Document 2: WO2013/094747 A1

SUMMARY OF THE INVENTION

Task to be Accomplished by the Invention

When a user who is incapable of a symmetric walking motion, in terms of space and/or time, owing to the disablement of one of the lower limbs wears the walking assist device, the motion of the disabled lower limb involves a smaller stroke and lacks in cyclic tendencies so that some difficulty often arises in estimating the phase of the motion of the lower limbs. When an assist force (torque) based on an inaccurate estimation of the phase of the motion of the lower limbs is applied to the user, the assist force may not completely match the motion of the lower limbs of the user so that the gait of the user may even be destabilized.

Patent Documents 1 and 2 do not contain any specific reference to a case of an asymmetric disability. The motion assist devices disclosed in these Patent Documents are configured to estimate the phase from data obtained by measuring the motion of each joint. Therefore, when such a motion assist device is applied to a user with an asymmetric disability, the phase of the motion of the disabled body lower limb cannot be correctly determined so that an optimum assist force cannot be produced.

One may try to assist the non-cyclic motion of the disabled lower limb of a user with an asymmetric disability according to the cyclic motion of the healthy lower limb of the user. In other words, even in the case of a user with an asymmetric disability, as long as the motion of the healthy lower limb is cyclic, and the phase of the motion of the health limb can be accurately determined, the necessary assist force may be computed based on the assumption that the phase of the disabled lower limb is displaced from the phase of the health lower limb by 180 degrees.

However, this method requires the knowledge regarding which of the lower limbs is healthy, and this information is required to be supplied to the motion assist device in advance.

In view of such problems of the prior art, a primary object of the present invention is to provide a walking assist device which can provide an appropriate cyclic assistance to a user with an asymmetric disability without requiring any complex parameter setting.

Means to Accomplish the Task

To achieve such an object, the present invention provides a walking assist device including a main frame (2) configured to be worn by a user, a power unit (2) mounted on the main frame, a pair of power transmission members (3L, 3R) pivotally attached to the main frame so as to be rotatable about respective hip joints of the user and to transmit assist force provided by the power unit to femoral parts of the user and a control unit (5) for controlling an operation of the power unit, wherein the control unit comprises a differential angle computation unit (21) for computing a differential angle ($\theta$) between angular positions of the femoral parts of the user about respective hip joints of the user; a differential angle phase computation unit (22) for computing a differential angle phase ($\Phi$) according to the differential angle; and an assist force computation unit (23) for computing an assist force ($\tau$) to be applied to the user according to the differential angle phase.

By thus making use of the differential angle between the left and right hip joint angles, irrespective of whether the user is a healthy person or a person with an asymmetric disability, and irrespective of which of the user's legs is disabled, because a cyclic motion can be extracted from the differential angle containing a component of the motion of the healthy leg having a large movable range of the hip joint to a large extent, the phase of the walking motion can be appropriately computed without requiring any complex parameter setting, and a cyclic assist force that meets the need of the user can be applied to the user with an appropriate timing even when the user has an asymmetric disability.

In this invention, it may be arranged such that the differential angle phase computation unit (22) comprises a differential angular speed computation unit (32) for computing a differential angular speed ($\omega$) according to the differential angle; a differential angular speed normalization unit (33) for normalizing the differential angular speed; a differential angle normalization unit (34) for normalizing the differential angle; and an inverse tangent computation unit (35) for computing the differential angle phase by performing an inverse tangent computation on the differential angle ($\theta n$) normalized by the differential angle normalization unit and the differential angular speed ($\omega n$) normalized by the differential angular speed normalization unit.

In this invention, the differential angle phase computation unit (22) may comprise a differential angle normalization unit (34) for normalizing the differential angle; and a map unit (91) for determining the differential angle phase according to the normalized differential angle ($\theta n$) by using a map defining a relationship between the differential angle phase and the normalized differential angle.

In this invention, the differential angle phase computation unit (22) may comprise a filter unit (31, 36) for filtering at least one of the differential angle and the differential angle phase; a walking frequency estimation unit (37) for estimating a walking frequency according to the differential angle; a phase delay estimation unit (38) for estimating a phase delay (dp) caused by the filter unit according to the walking frequency; and a phase delay compensation unit (39) for compensating the phase delay of the differential angle phase according to the estimated phase delay.

According to this arrangement, the noises such as those created by the feet impacting the floor surface that may be contained in the differential angle can be canceled by the filter unit so that a phase estimation of a high accuracy can be achieved. Also, when the phase delay that is caused by the filter unit is compensated, the walking motion of the user can be assisted with an even higher accuracy.

In this invention, the assist force computation unit (23) may comprise an oscillator phase arithmetic operation unit (24) for computing a phase of an oscillator that oscillates in synchronism with the differential angle phase, and an assist force determination unit (25) for determining the assist force according to the oscillator phase (Φc) computed by the oscillator phase computation unit.

Thereby, even when the differential angle undergoes rapid changes or continues to fluctuate for long periods of time, the differential angle phase is corrected so as to change at a constant rate according to the autonomous oscillation of the oscillator.

In this invention, the oscillator phase computation unit may comprise an oscillator natural angular frequency computation unit (41) for computing a natural angular frequency (ω0) of a phase oscillator corresponding to the walking frequency (freq) of the user determined from the differential angle; and a phase oscillator integration computation unit (42) for computing the oscillator phase (Φc) by performing an integration computation on a phase change of the phase oscillator by taking into account a phase difference (Φ−Φc) between the differential angle phase and the oscillator phase.

In this invention, the oscillator natural angular frequency computation unit may be configured to compute the natural angular frequency of the phase oscillator by using the walking frequency determined from the differential angle.

In this invention, the assist force determination unit (25) may comprise an assist phase computation unit (51) for computing, from the differential angle phase (Φas), an assist force phase adjusted to cause the assist force to be produced at an appropriate timing; and a right and a left assist force computation unit (52) for computing assist forces (τL, τR) for the femoral parts of the user according to an assist force phase.

According to this arrangement, the assist force can be produced with a phase property that is most effective in assisting the walking motion of the user.

In this invention, the assist force determination unit may comprise a left assist phase computation unit (111L) for adjusting the differential angle phase so as to be a left assist force phase (ΦasL) that allows the assist force for the left femoral to be produced at an appropriate timing; a left assist force computation unit (112L) for computing the left assist force (τL) according to the left assist force phase; a right assist phase computation unit (111R) for adjusting the differential angle phase so as to be a right assist force phase (ΦasR) that allows the assist force for the right femoral to be produced at an appropriate timing; and a right assist force computation unit (112R) for computing the right assist force (τR) according to the right assist force phase.

According to this arrangement, because the left and right assist forces can be computed individually, the walking motion of the user can be assisted in a smooth manner by providing a difference between the left and right assist forces by taking into account the difference between the conditions of the two legs of the user.

Effect of the Invention

Thus, the present invention provides a walking assist device that can provide an appropriate cyclic assistance to a user without requiring any complex parameter setting even when the user suffers from an asymmetric disability.

DESCRIPTION OF THE PREFERRED EMBODIMENT(S)

Preferred embodiments of the present invention are described in the following with reference to the appended drawings.

First Embodiment

Figure 1:
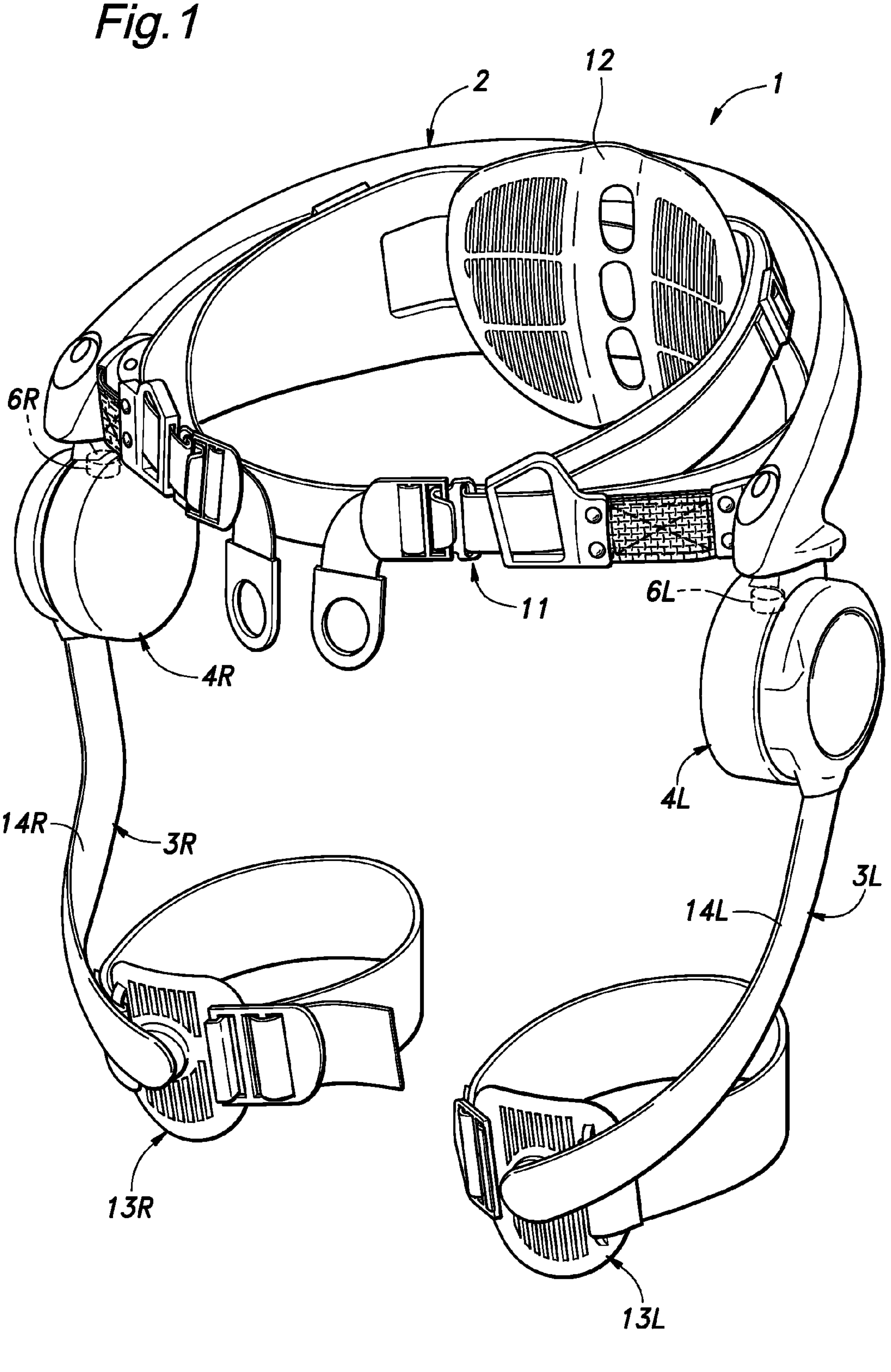
FIG. 1 is a perspective view of a walking assist device given as a first embodiment of the present invention.

As shown in FIG. 1, the walking assist device 1 of the first embodiment includes a main frame 2 configured to be worn on a pelvic part of the user P, a pair of femoral support units 3 (3L and 3R) pivotally attached to either side part of the main frame 2 at the positions corresponding to the hip joints of the user P at the base ends thereof via respective power units 4, a control unit 5 (See FIG. 3) for controlling the operation of the power units 4, a pair of angular position sensors 6 for detecting the angles of the femoral support units 3 provided at the respective pivoted base ends of the femoral support units 3 with respect to the main frame 2 and a battery (not shown in the drawings) for supplying electric power to the power units 4 and the control unit 5.

The main frame 2 is made of a combination of stiff material such as hard plastics and metals and flexible material such as fabrics and foamed plastics, and is secured to the pelvic part of the user P by a belt 11 detachably connected between the opposite ends of the main frame 2 on the front side of the user P. A flexible back support plate 12 is provided on the front side of the rear part of the main frame 2 to provide a flexible support for the back side of the user P.

The femoral support units 3 each consist of an arm member 14 and a femoral retainer 13. Each arm member 4 is made of stiff material such as hard plastics and metals, and extends along the length of the femoral part of the user P. Each femoral retainer 13 is made of a combination of stiff material and flexible material, and is configured to the detachably worn on the lower femoral part of the user P. Thus, each arm member 14 connects the corresponding femoral retainer 13 to an output shaft of the corresponding power unit 4.

Each power unit 4 is incorporated with an electric motor, and may additionally include a speed reduction mechanism and/or a compliance mechanism. By receiving electric power supplied by the battery via the control unit 5, each power unit 4 angularly drives the corresponding arm member 14, and assists the movement of the femoral part of the user P via the corresponding femoral retainer 13.

Each angular position sensor 6 consists of an absolute angle sensor provided in association with the corresponding power unit 4, and produces a signal corresponding to the femoral angle θL, θR of the femoral part of the user P with respect to the coronal plane of the user P. The signals from the angular position sensors 6 are forwarded to the control unit 5.

Figure 2:
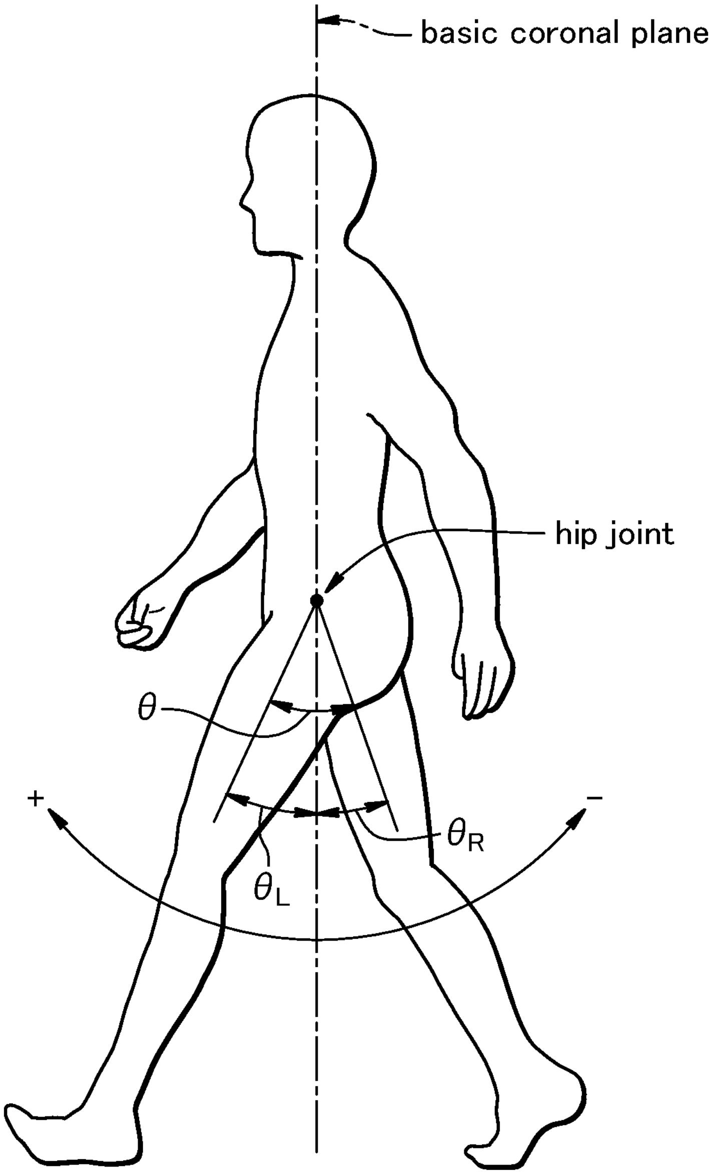
FIG. 2 is a diagram showing the definition of the hip joint angle and the differential angle.

As shown in FIG. 2, the femoral angle θL, θR is defined as being positive when the femoral part is ahead of the coronal plane or bent, and negative when the femoral part is behind the coronal plane or extended.

The battery is received in or attached to the main frame 2, and supplies electric power to the control unit 5 and the power units 4. The control unit 5 is received in or attached to the main frame 2. The battery and/or the control unit 5 may also be provided separately from the walking assist device 1.

The control unit 5 consists of an electronic circuit unit including CPU, RAM, ROM and a peripheral circuit, and is programmed to execute required computational processes by reading out commands and necessary data from a storage unit (memory) not shown in the drawings. The control unit 5 thereby controls the operation of the power units 4 and hence the assist force that is applied to the femoral parts of the user P.

The walking assist device 1 is thus configured to assist the walking movement of the user P by applying the power of the power units 4 to the femoral parts of the user P via the main frame 2 and the femoral support units 3.

Figure 3:
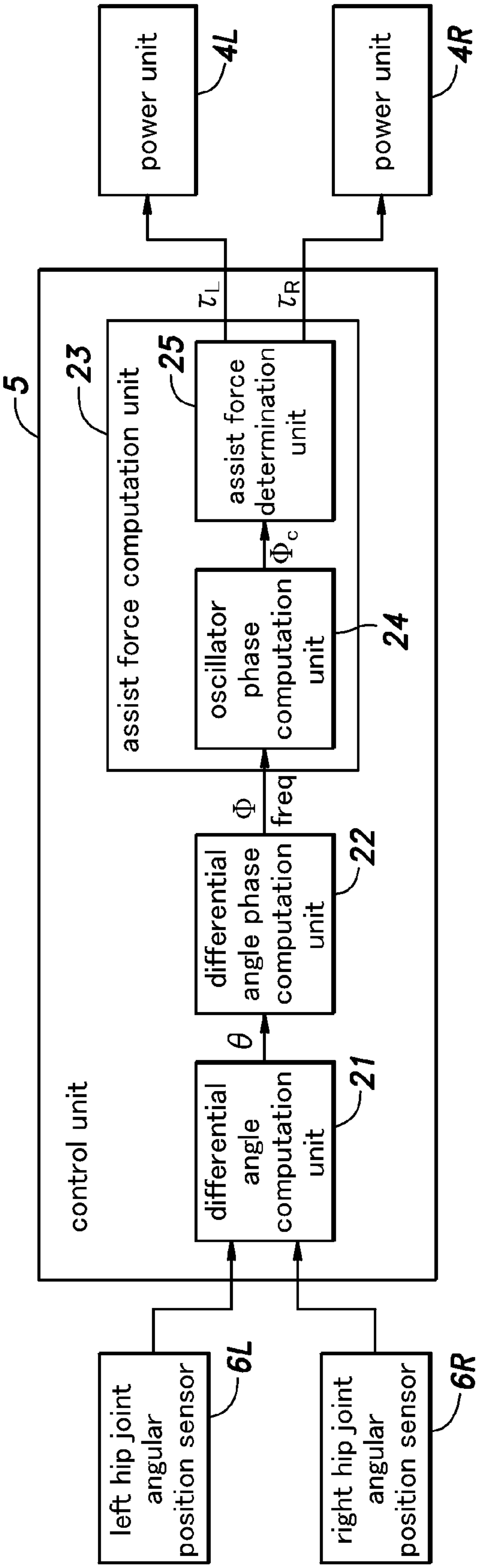
FIG. 3 is a block diagram of the control unit.

As shown in FIG. 3, the control unit 5 includes a differential angle computation unit 21 for computing the differential angle θ given as the difference between the right and left femoral angles θL and θR by executing a computational process (which will be described hereinafter) based the detected femoral angles θL and θR, a differential angle phase computation unit 22 for computing a differential angle phase Φ and a walking frequency freq by executing a computation process (which will be described hereinafter) based on the differential angle θ computed by the differential angle computation unit 21, and an assist force computation unit 23 for computing an assist force τ by executing a computational process (which will be described hereinafter) based on the differential angle phase Φ computed by the differential angle phase computation unit 22.

The assist force computation unit 23 includes an oscillator phase computation unit 24 for computing the oscillator phase of a phase oscillator that oscillate in synchronism with the differential angle phase Φ by executing a computation process using a phase oscillator corresponding to the walking frequency freq of the user P wearing the walking assist device 1 based on the walking frequency freq and the differential angle phase computed by the differential angle phase computation unit 22, and an assist force determination unit 25 for computing the assist forces τ for the two femoral parts of the user P by executing a computational process (which will be described hereinafter) based on the oscillator phase Φc computed by the oscillator phase computation unit 24.

When powered up, the control unit 5 drives the power units 4L and 4R so as to produce the assist forces τL and τR determined from the outputs of the angular position sensors 6L and 6R.

The differential angle computation unit 21 computes the differential angle θ between the two femoral parts by subtracting one of the femoral angles (right femoral angle) θR from the other femoral angle (left femoral angle) θL, or by the following equation (1).

$$\theta = \theta L - \theta R \quad (1)$$

Thus, the differential angle θ is given as the angle of the left femoral part relative to the right femoral part, and is positive in sign when the left femoral part is ahead of the right femoral part (or is bent), and negative in sign when the left femoral part is behind the right femoral part (or is extended). When the user P has stood up or has squatted with the two femoral parts aligned with each other, the two femoral angles θL and θR are equal to each other so that the differential angle θ is zero. Likewise, the differential angular speed ω which is given as the time differential of the differential angle θ is positive in sign when the left femoral part is bent and the right femoral part is extended, and negative in sign when the left femoral part is extended and the right femoral part is bent. The differential angle computation unit 21 executes the computational process mentioned above at a prescribed computational cycle of the control unit 5.

Instead of using the two angular position sensors 6L and 6R for measuring the femoral angles, it is also possible to provide a sensor in the main frame 2 to detect the relative angle between the right and left femoral support units 3L and 3R, and to have the differential angle computation unit 21 use the output signal of this sensor as the differential angle between the two femoral parts of the user. It is also possible to use an IMU including an acceleration sensor and a gyro sensor for measuring the attitudes of the two femoral parts of the user, and obtain the differential angle θ as the difference between the angles of the two femoral parts with respect to the vertical line as projected onto the sagittal plane.

The differential angle phase computation unit 22 shown in FIG. 3 is described in the following. As shown in the block diagram of FIG. 4, the differential angle phase computation unit 22 includes various functional units 31 to 39 for executing the computational and other processes which will be described hereinafter. The functional units of the differential angle phase computation unit 22 execute these processes at a prescribed computational cycle of the control unit 5. Each of these functional units is described in the following.

First of all, the differential angle phase computation unit 22 executes the process of a first low pass filter 31 at each computational process cycle.

Figure 5A:
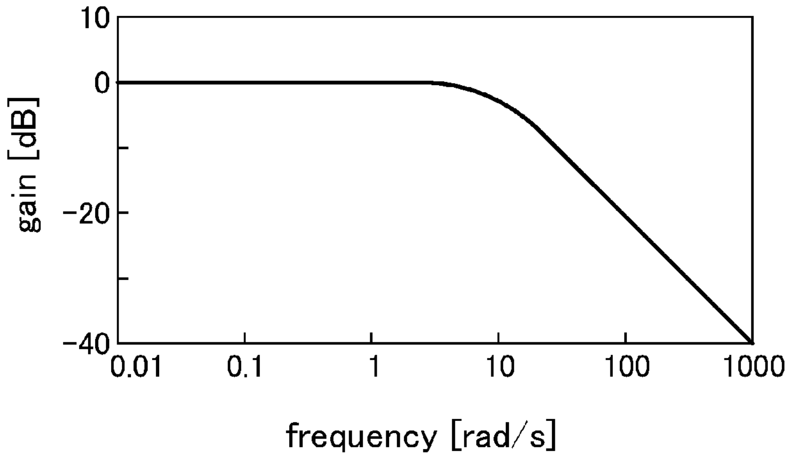
FIG. 5 is a Bode diagram of the first low pass filter shown in FIG. 4.
Figure 5B:
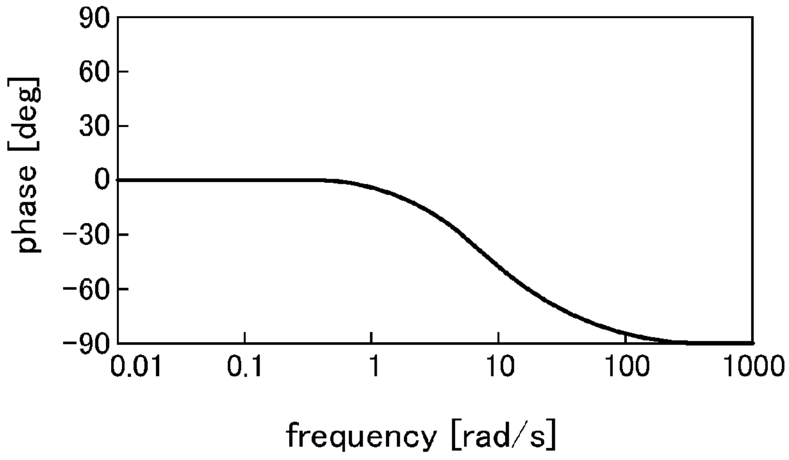

The first low pass filter 31 performs a low pass filter (high cut) process consisting of shutting off a high frequency component of the signal corresponding to the differential angle θ computed by the differential angle computation unit 21. FIG. 5 shows a Bode diagram of the first low pass filter 31. As shown in the gain diagram of FIG. 5A, the cutoff frequency (2 to 3 Hz) of the first low pass filter 31 is preferably higher than the expected walking frequency of the user P. As shown in the phase diagram of FIG. 5B, the differential angle θf that has passed the first low pass filter 31 is given with a prescribed phase property $\phi 1f$ (freq) that can be represented as a mathematic function of frequency.

Figure 4:
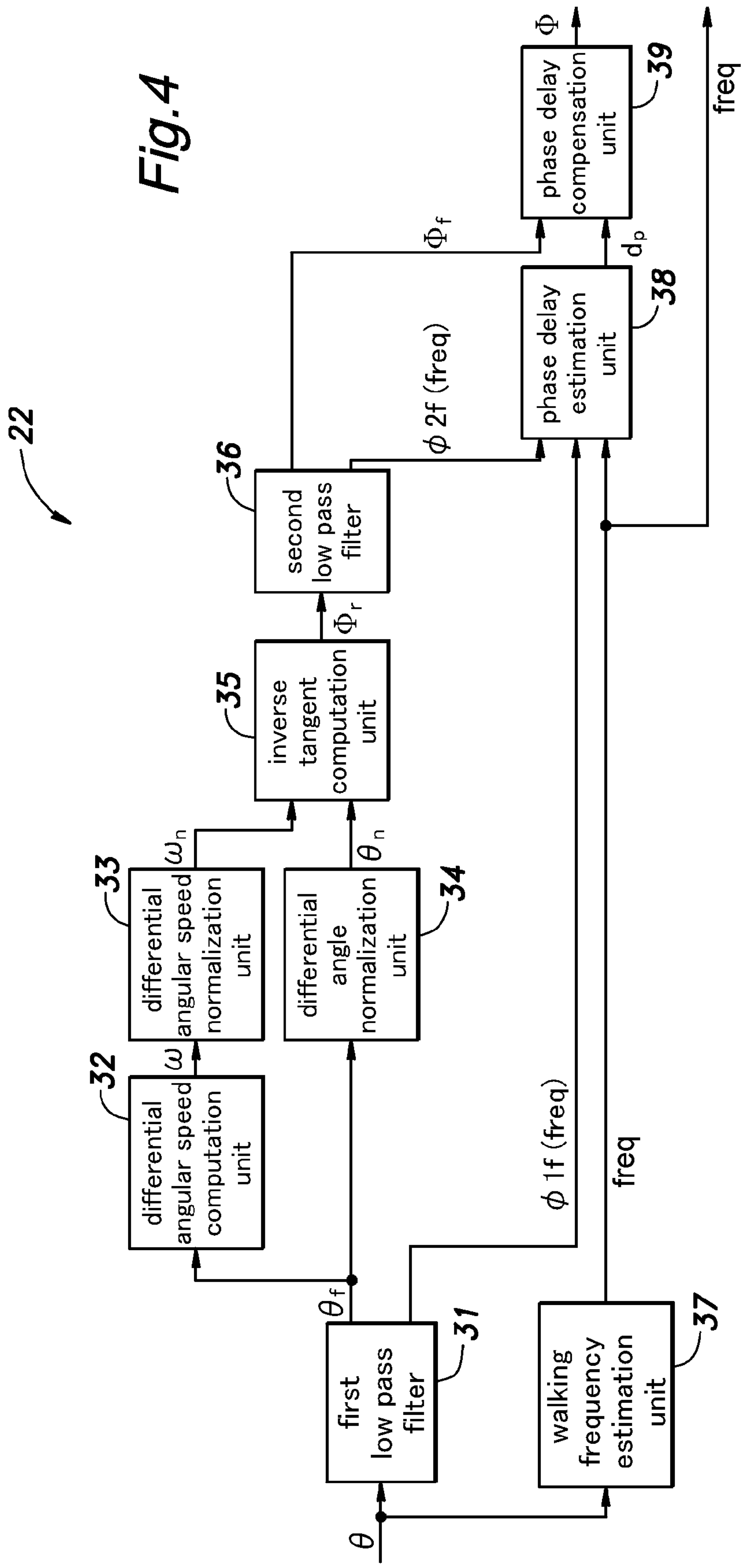
FIG. 4 is a block diagram of the differential angle phase computation unit shown in FIG. 3.

Following the execution of the process of the first low pass filter 31, the differential angle phase computation unit 22 executes the process of a differential angular speed computation unit 32 shown in FIG. 4.

Based on the differential angle θf, the differential angular speed computation unit 32 computes a differential angular speed ω. More specifically, the differential angular speed computation unit 32 computes the differential angular speed ω by performing the computation of Equation (2) given in the following:

$$\omega=(\theta f\_N-\theta f\_N-1)/Tc \quad (2)$$

where θf_N is the differential angle θf computed in the current computation cycle, θf_N−1 is the differential angle θf computed in the previous computational cycle, and Tc is the computational cycle period.

After executing the process of the differential angular speed computation unit 32, the differential angle phase computation unit 22 executes the process of a differential angular speed normalization unit 33 shown in FIG. 4.

The differential angular speed normalization unit 33 normalizes the differential angular speed ω according to a prescribed rule based on the maximum value and the minimum value of the differential angular speed ω in the preceding walking cycle, and produces a normalized differential angular speed ωn. More specifically, the differential angular speed normalization unit 33 computes the differential angular speed ω by performing the computation of Equation (3) given in the following.

$$\omega n=(\omega-(\omega MAX+\omega MIN)/2)/\{(\omega MAX-\omega MIN)/2\} \quad (3)$$

where ωMAX is the maximum value of the differential angular speed ω in the preceding walking cycle, and ωMIN is the minimum value of the differential angular speed ω in the preceding walking cycle.

The numerator of the normalized differential angular speed ωn represented in Equation (3) indicates that the offset of the differential angular speed ω is removed so that the absolute values of the positive peak and the negative peak of the differential angular speed ω are equal to each other, and the denominator indicates the amplitude of the differential angular speed ω in the preceding step of the walking movement. Therefore, the differential angular speed ω is normalized by the differential angular speed normalization unit 33 executing the computation of Equation (3) at the same time as the user P walks.

Following the process of the first low pass filter 31, the differential angle phase computation unit 22 performs the process of a differential angle normalization unit 34 shown in FIG. 4.

The differential angle normalization unit 34 normalizes the differential angle θf that has been processed by the first low pass filter 31 according to a prescribed rule based on the maximum value and the minimum value of the differential angle θ in the preceding walking cycle, and produces a normalized differential angle θn. More specifically, the differential angle normalization unit 34 computes the differential angle θ by performing the computation of Equation (4) given in the following.

$$\theta n=(\theta-(\theta MAX+\theta MIN)/2)/\{(\theta MAX-\theta MIN)/2\} \quad (4)$$

where θMAX is the maximum value of the differential angle θ in the preceding walking cycle, and θMIN is the minimum value of the differential angle θ in the preceding walking cycle.

The numerator of the normalized differential angle θn in Equation (4) represents the removal of the offset which performed in such a manner that the positive peak and the negative peak of the differential angle θ in the previous cycle of the walking motion are equal to each other, and the denominator represents the amplitude of the differential angle θ in the previous cycle of the walking motion. Therefore, by performing the computation of Equation (4) with the differential angle normalization unit 34, the differential angle θf is normalized according to the walking motion of the user P.

Following the processes executed by the differential angle normalization unit 34 and the differential angular speed normalization unit 33, the differential angle phase computation unit 22 performs of the process of an inverse tangent computation unit 35.

Based on the normalized differential angle θn normalized by the differential angle normalization unit 34 and the normalized differential angular speed con normalized by the differential angular speed normalization unit 33, the inverse tangent computation unit 35 computes a differential angle phase Φr by executing an inverse tangent computation. More specifically, by performing the computation of Equation (5) given in the following, the inverse tangent computation unit 35 computes the differential angle phase Φr in the phase plane of the normalized differential angle θn and the normalized differential angular speed ωn as shown in FIG. 4).

$$\Phi r=\arctan(\omega n/\theta n) \quad (5)$$

Figure 6:
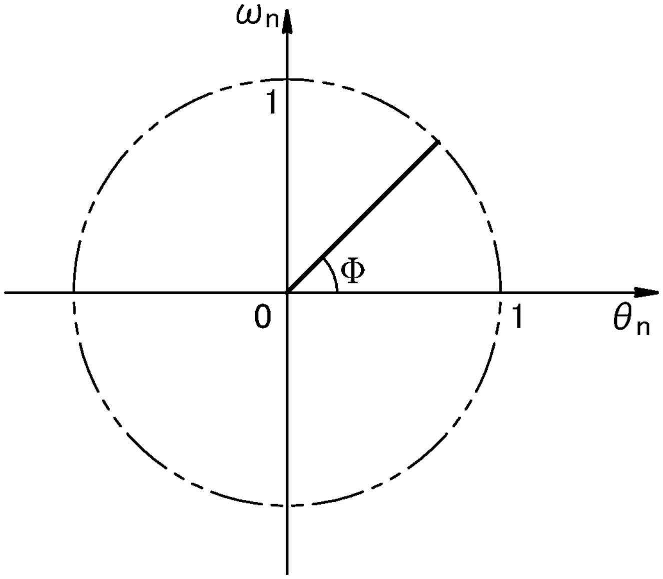
FIG. 6 is a diagram illustrating the differential angle phase.

The differential angle phase Φr computed by Equation (5) represents the progress of the walking motion of a basic cycle consisting of two steps made by the left and right legs one after the other as schematically illustrated in the phase plane of FIG. 6.

After executing the process of the inverse tangent computation unit 35, the differential angle phase computation unit 22 executes the process of a second low pass filter 36.

The second low pass filter 36 executes a low pass (high cut) process consisting of shutting off a high frequency component from a signal corresponding to the differential angle phase Φr computed by the inverse tangent computation unit 35, and permitting the passage of a low frequency component. The cut off frequency of the second low pass filter 36 is preferably set to a frequency (0.5 Hz to 1 Hz) higher than the range of the walking frequency freq which is normally associated with the walking motion of the user P, as opposed to the first low pass filter 31. The differential angle phase Φr that has passed through the second low pass filter 36 is provided with a phase property ϕ2*f* (freq) which is a mathematical function of the walking frequency.

The differential angle phase computation unit 22 executes a process of a walking frequency estimation unit 37 simultaneously as the above mentioned process in each computation cycle of the control unit 5.

The walking frequency estimation unit 37 estimates the walking frequency freq from the differential angle θ. For instance, the walking frequency estimation unit 37 computes the walking frequency freq by using a high speed Fourier transformation or a wavelet transformation. When the walking frequency freq is computed by the walking frequency estimation unit 37, window functions are multiplied to each other. The interval of the window functions may be selected so as to contain the differential angle θ for a plurality of steps.

After executing the process of the walking frequency estimation unit 37 and the process of the second low pass filter 36, the differential angle phase computation unit 22 executes a process of a phase delay estimation unit 38.

The phase delay estimation unit 38 estimates a phase delay dp according to the phase property ϕ2*f* (freq) of the differential angle phase Φr that has passed through the second low pass filter 36, the phase property ϕ1*f* (freq) of the differential angle θ that has passed through the first low pass filter 31 and the walking frequency freq computed by the walking frequency estimation unit 37. The phase delay dp can computed by Equation (6) given in the following.

$$dp=\phi 1f(\mathrm{freq})+\phi 2f(\mathrm{freq}) \quad (6)$$

The differential angle phase computation unit 22 then executes the process of a phase delay compensation unit 39. The phase delay compensation unit 39 corrects the differential angle phase Φf that has passed through the second low pass filter 36 in dependence on the phase delay dp computed by the phase delay estimation unit 38, and produces the corrected differential angle phase Φ. More specifically, the differential angle phase computation unit 22 computes the differential angle phase Φ by executing the computation consisting of subtracting the phase delay dp from the differential angle phase Φr as represented by Equation (7) given in the following.

$$\Phi=\Phi r-dp \quad (7)$$

The oscillator phase computation unit 24 of the illustrated embodiment shown in FIG. 3 is described in the following with reference to the block diagram shown in FIG. 7. The oscillator phase computation unit 24 includes functional blocks consisting of an oscillator natural angular frequency computation unit 41 and a phase oscillator integration computation unit 42 for executing the computations or processes discussed in the following. The oscillator phase computation unit 24 executes the processes of these functional blocks 41 and 42 at the prescribed computational cycle of the control unit 5.

The oscillator natural angular frequency computation unit 41 computes an oscillator natural angular frequency ω0 or the natural frequency of the oscillator according to the walking frequency freq estimated by the walking frequency estimation unit 37 shown in FIG. 4. More specifically, the oscillator natural angular frequency computation unit 41 computes the oscillator natural angular frequency ω0 by executing the computation represented by Equation (8) given in the following.

$$\omega 0=2\pi\times\mathrm{freq} \quad (8)$$

The oscillator natural angular frequency ω0 computed by Equation (8) is a variable based on the walking frequency freq of the user P of the walking assist device 1, but may also consist of a constant value assigned to the oscillator natural angular frequency computation unit 41 as a target walking frequency or may be obtained by applying a low pass filter to the walking frequency freq.

After executing the process of the oscillator natural angular frequency computation unit 41, the differential angle phase computation unit 22 executes the process of a phase oscillator integration computation unit 42.

The phase oscillator integration computation unit 42 produces an oscillator phase Φc of a phase oscillator which oscillates in synchronism with the differential angle phase Φ according to the natural angular frequency ω0 of the oscillator by using the differential angle phase Φ corrected by the phase delay compensation unit 39 shown in FIG. 4 as an input. More specifically, the phase oscillator integration computation unit 42 computes the oscillator phase Φc associated with the synchronized oscillation by solving the differential equation represented by Equation (9) given in the following or by performing an integration computation on the phase change of the phase oscillator corresponding to the natural angular frequency ω0 by taking into account the phase difference between the differential angle phase Φ and the phase oscillator.

$$d\Phi c/dt=\omega 0+f(\Phi-\Phi c+\alpha) \quad (9)$$

where f(x) represents a mathematical function, and α is a prescribed phase difference for adjusting the oscillator phase Φc. Preferably, f(x) is a monotonously increasing function when x is near zero (when $-\pi/4<x<\pi/4$, for instance). For instance, f(x) may be represented by Equation (10) given in the following.

$$f(x)=K\sin(x) \quad (10)$$

where K is a constant.

The assist force determination unit 25 shown in FIG. 3 is described in the following. As shown in the block diagram of FIG. 8, the assist force determination unit 25 is provided with various functional units (51 and 52) for performing computations or processes which will be discussed hereinafter. The assist force determination unit 25 executes the processes of these functional units at the prescribed computational cycles of the control unit 5.

An assist phase computation unit 51 adjusts the oscillator phase Φc computed by the oscillator phase computation unit 24 so that the assist force τ may be produced at an appropriate timing. More specifically, the assist phase computation unit 51 computes an assist force phase Φ as by executing the computation represented by Equation (11) given in the following.

$$\Phi as=\Phi c-\beta \quad (11)$$

where β is an assist target phase difference. In other words, the assist phase computation unit 51 computes the assist force phase Φ as which is adjusted such that the assist force is produced at an appropriate timing by subtracting the assist target phase difference β (which is introduced for producing the assist force τ at an appropriate timing) from the computed oscillator phase Φc.

Following the process of the assist phase computation unit 51, the assist force determination unit 25 executes a right and left assist force computation unit 52.

The right and left assist force computation unit 52 computes the left and right assist forces τL and τR according to the assist force phase Φas of the differential angle θ. More specifically, the right and left assist force computation unit 52 performs the computations represented by Equations (12) and (13) given below.

$$\tau L = G \times \sin \Phi as \quad (12)$$

$$\tau R = -\tau L \quad (13)$$

where G is a gain constant which is set in dependence on the desired magnitude of the assist force, and can vary depending on the purpose and the condition of the user P of the walking assist device 1.

Alternatively, the right and left assist force computation unit 52 may determine the left assist force τL by looking up a map or a table that defines the relationship of the assist force between the assist force phase Φas as represented by Equation (14) given in the following.

$$\tau L = \mathrm{LUT}(\Phi as) \quad (14)$$

In this case, if the assist force defined by the map takes into account the assist target phase difference β, the left assist force τL may be obtained by the right and left assist force computation unit 52 by using the oscillator phase Φc as an input without requiring the assist phase computation unit 51 as represented by Equation (14) given in the following.

$$\tau L = \mathrm{LUT}(\Phi c) \quad (15)$$

The control unit 5 executes the above discussed processes at the prescribed computational cycle, and supplies electric power to the left and right power units 4L and 4R such that the computed left and right assist forces τL and τR may be produced, and the walking motion of the user P of the walking assist device 1 may be appropriately assisted.

Figure 9:
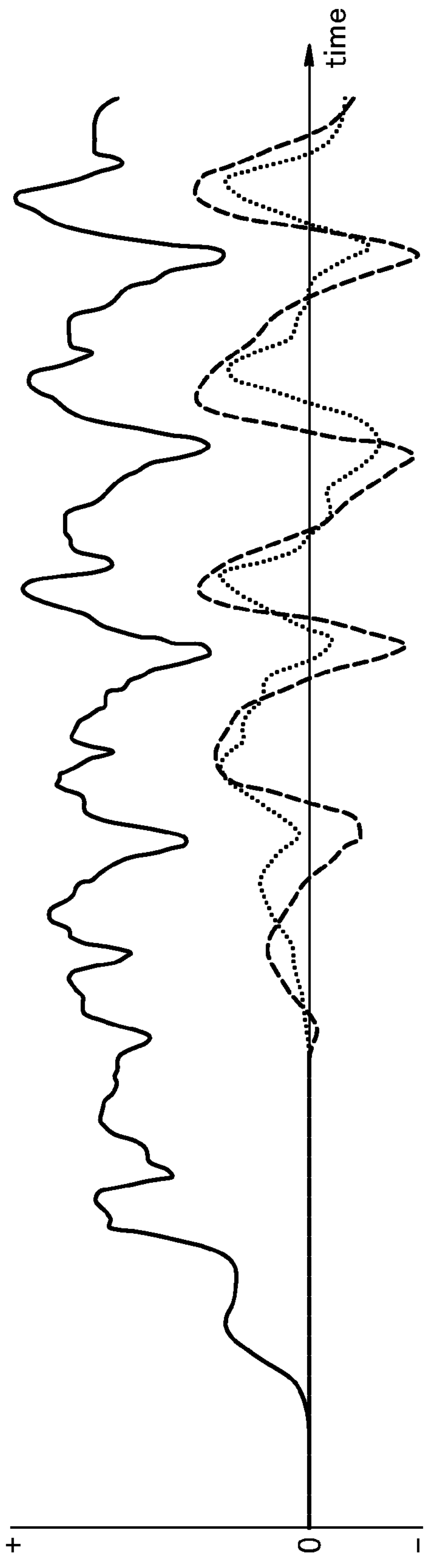
FIG. 9 is a time chart demonstrating an effect of the walking assist device of the first embodiment.

FIG. 9 is a time chart showing the estimated phase (dotted line) based on a conventional algorithm (that estimates the phase of the femoral part from the hip joint angle of the disabled side), the estimated phase (broken line) based on the algorithm of the illustrated embodiment and the pivot joint angle (solid line) of the disabled side in relation to the passage of time when the walking assist device is worn by a user with an asymmetric disability. In this time chart, the positive region (+) of the ordinate corresponds to the hip joint angle on the bent side, and the negative region (−) corresponds to the hip joint angle on the extended side.

In the case of a user P demonstrating a walking pattern as indicated by the solid line, the conventional method (dotted line) resulted in a poor performance in estimating the phase from the hip joint angle, and extending motion is mistaken for bending motion in some time intervals. Furthermore, the waveform of the estimated phase contains a significant amount of high frequency components. When extending motion is mistaken for bending motion, a torque opposing the motion of the femoral part (instead of a torque assisting the motion of the femoral part) is produced. An excessive amount of high frequency components causes discomfort to the user.

On the other hand, according to the illustrated embodiment, as indicated by the broken line, the extending motion and the bending motion are estimated to take place in an alternating manner in synchronism with the frequency of the walking motion. Therefore, the assist torque can be produced at an appropriate timing in relation to the extending motion and the bending motion of the user P so that a smooth assisting action can be accomplished.

Thus, according to the control unit 5 of the illustrated embodiment, as shown in FIG. 3, the differential angle computation unit 21 computes the differential angle θ between the hip joint angles of the left and right legs of the user P, the differential angle phase computation unit 22 computes the differential angle phase Φ according to the computed differential angle θ, and the assist force computation unit 23 computes the assist force τ that is to be applied to the user P according to the computed differential angle phase Φ. Therefore, not only when the walking assist device is worn by a healthy person but also when the walking assist device is worn by a user with an asymmetric disability, because a cyclic motion can be extracted from the healthy leg which has a greater range of angular movement about the hip joint than the disabled leg, the differential angle phase Φ of the walking motion can be extracted without requiring any complex parameter settings, and an assist force τ that is suitable for the user P can be produced.

In other words, even when the motion of the disabled leg is not cyclic or when the motion of the disabled leg is cyclic, but involves significant fluctuations, the conventional method was unable to produce an assist force at an optimum timing. On the other hand, according to the illustrated embodiment, by using the differential angle θ between the two legs about the respective hip joints, the differential angle phase Φ of the walking motion can be estimated in a stable manner so that the assist force τ can be applied to the legs of the user P at an optimum timing.

The walking assist device 1 of the illustrated embodiment can provide an assist force τ at an appropriate timing with a same algorithm and without requiring extensive changes in parameter settings not only to severely impaired users such as those with an asymmetric disability in acute phase, those with a non-cyclic walking pattern and those with a severe asymmetric disability but also to mildly impaired users such as those in a rehabilitation stage, healthy persons and those with a mild symmetric disability.

When the left and right hip joints undergo a same phase motion such as when the user attempts a bowing movement, the conventional device typically produces a walking assist force even though the user does not intend to walk. However, when the differential angle θ is used as in the case of the present invention, because the differential angle θ that is used for the computation of the assist force remains unchanged in such a case, no unnecessary assist force τ is produced so that the assist force τ is applied to the user only when the user is walking, without requiring any special process to be executed.

The differential angle phase computation unit 22 comprises the first low pass filter 31 for filter processing the differential angle θ and the second low pass filter 36 for filter processing the differential angle phase Φ, and estimates the walking frequency freq with the walking frequency estimation unit 37 based on the differential angle θ. The differential angle phase computation unit 22 further estimates the phase delay dp caused by the two low pass filters 31 and 36 based on the walking frequency freq, and compensates the phase delay of the differential angle phase Φr with the phase delay estimation unit 38 based on the phase delay dp. Thereby, the noises that may be contained in the differential angle θ is canceled by the first low pass filter 31 so that the accuracy in estimating the differential angle phase with the inverse tangent computation can be improved. Meanwhile, because the first low pass filter 31 is a filter for the differential angle θ, the cutoff frequency of the first low pass filter 31 is required to be relatively high. Therefore, the first low pass filter 31 may not adequately eliminate estimation errors by itself. By applying the second low pass filter 36 to the differential angle phase Φr, a low pass filter with a relatively low cutoff frequency can be applied so that the accuracy in estimating the phase can be improved. Moreover, because the phase delay due to the first and second low pass filters 31 and 36 is compensated, even though a filter with a low cutoff frequency is applied, the walking motion of the user P wearing the walking assist device 1 can be assisted with a high precision without involving a delayed assist phase.

As shown in FIG. 3, in the oscillator phase computation unit 24, the oscillator phase Φc that oscillates in synchronism with the differential angle phase Φ is computed from the natural angular frequency ω0 corresponding to the walking frequency freq of the user P that is obtained from the differential angle θ. In the assist force determination unit 25, the assist force computation unit 23 is configured such that the assist force τ is determined from the oscillator phase Φc computed by the oscillator phase computation unit 24. Thus, even when the differential angle phase Φ makes a sharp change or continues to fluctuate, because the change of the differential angle phase Φ is corrected so as to occur at a constant speed according to the autonomous oscillation of the phase oscillator with the result that the assist force τ is produced with an appropriate phase.

Figure 8:
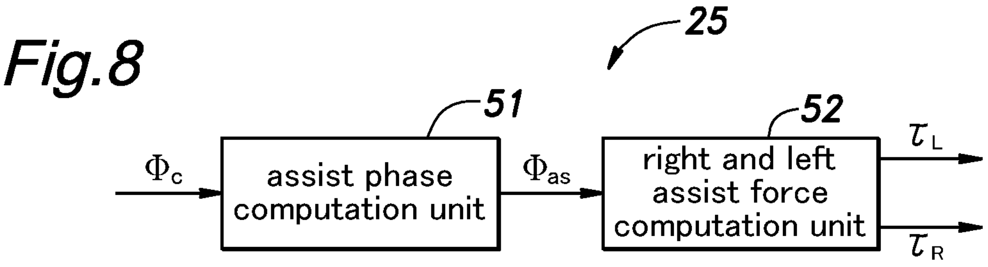
FIG. 8 is a block diagram of the assist force determination unit shown in FIG. 3.

As shown in FIG. 8, the assist force determination unit 25 is configured such that the oscillator phase Φc is adjusted so as to be the assist force phase Φas that causes the assist force τ to be produced at an appropriate phase by the assist phase computation unit 51, and the left and right assist forces τL and τR are computed from the assist force phase Φas that is adjusted by the assist phase computation unit 51 by the right and left assist force computation unit 52.

Second Embodiment

A second embodiment of the present invention is described in the following with reference to FIG. 10.

Figure 10:
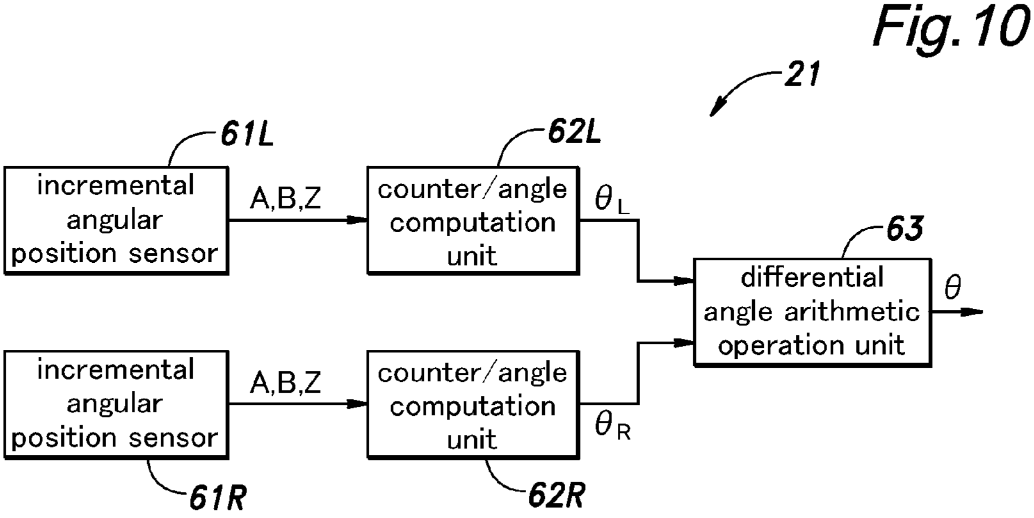
FIG. 10 is a block diagram of the differential angle computation unit of a second embodiment.

FIG. 10 shows a modification of the differential angle computation unit 21 of the walking assist device 1 of the first embodiment shown in FIG. 3. The structure and the functions of the second embodiment are otherwise similar to those of the first embodiment. Therefore, the parts corresponding to those of the first embodiment are omitted, and only those parts that are different from the counterparts in the first embodiment are described in the following. The same is true with other embodiments that are described later.

In this embodiment, instead of using absolute type angular sensors for the hip joint angular position sensors 6L and 6R of the first embodiment, incremental type angular sensors 61L and 61R for detecting the angles of the femoral parts relative to the main frame 2 are used as shown in FIG. 10. The differential angle computation unit 21 computes the differential angle θ from the outputs of these incremental type angular sensors 61L and 61R.

The differential angle computation unit 21 is provided with counter/angle computation units 62L and 62R for computing the hip joint angles θL and θR corresponding to the angles of the respective sub frames or the femoral support units 3L and 3R relative to the main frame 2 from the signals produced from the incremental type angular sensors 61L and 61R and a differential angle arithmetic operation unit 63 for computing the differential angle θ between the two femoral parts of the user P from the respective hip joint angles θL and θR computed by the counter/angle computation units 62L and 62R. The differential angle arithmetic operation unit 63 computes the differential angle θ by executing Equation (1) given above similarly as the first embodiment.

The walking assist device 1 is modified from the first embodiment in this regard, but provides similar action and effects as the first embodiment. Alternatively, instead of the incremental type angular sensors 61L and 61R, a plurality of Hall sensors may be provided on each side of the user P so that the hip joint angles θL and θR of the respective femoral parts may be computed from the magnetic signals or Hall state signals provided by the Hall sensors.

Third Embodiment

Figure 11:
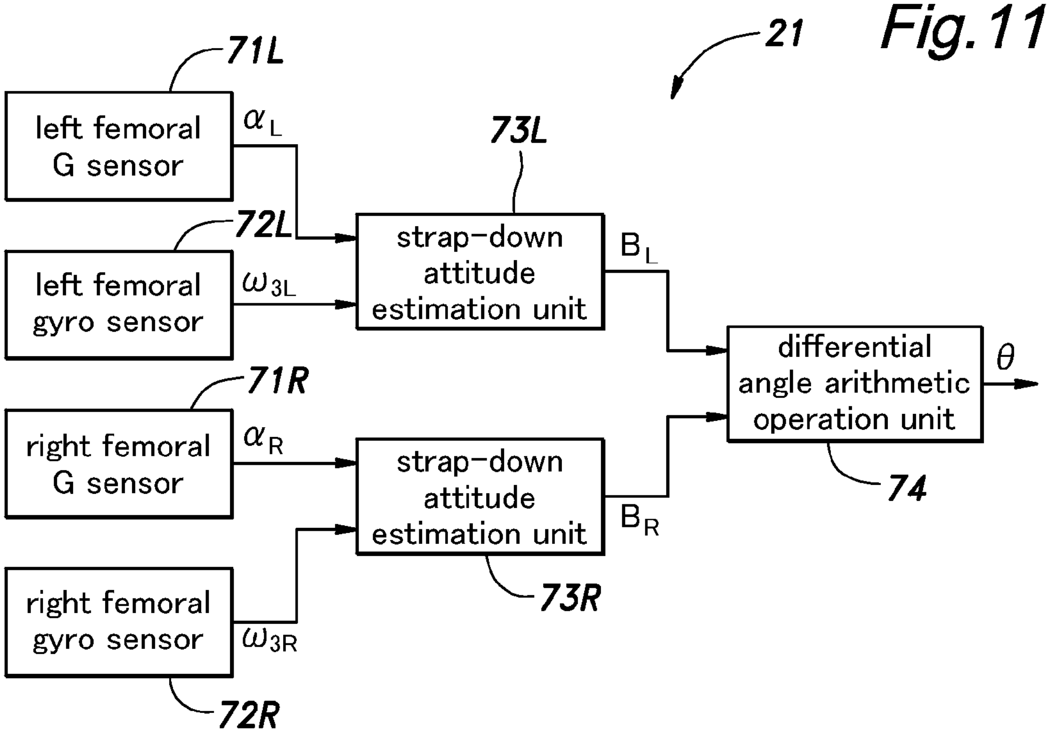
FIG. 11 is a block diagram of the differential angle computation unit of a third embodiment.

FIG. 11 shows the structure of the differential angle computation unit 21 in a third embodiment of the present invention.

In this embodiment, the walking assist device 1 is provided with a left femoral G sensor 71L and a right femoral G sensor 71R for detecting the fore and aft accelerations of the respective femoral support units 3L and 3R, and a left femoral gyro sensor 72L and a right femoral gyro sensor 72R for detecting the angular speeds ω3L and ω3R of the respective femoral support units 3L and 3R, instead of the hip joint angular position sensors 6L and 6R of the first embodiment. The differential angle computation unit 21 computes the differential angle θ from the output signals provided by these sensors 71L, 71R, 72L and 72R.

The differential angle computation unit 21 is provided with a left and right strap-down attitude estimation units 73L and 73R for estimating the respective attitude angle vectors BL and BR by executing a strap-down attitude estimation computation based on the detection signals of the femoral G sensors 71L and 71R and the femoral gyro sensors 72L and 72R, and a differential angle arithmetic operation unit 73 for computing the differential angle θ between the two femoral parts of the user P from the attitude angle vectors BL and BR estimated by the respective strap-down attitude estimation units 73L and 73R. Each strap-down attitude estimation unit 73 executes the per se known strap-down attitude estimation computation, and uses only the parameters associated with the motion of the femoral parts on the sagittal plans. The walking assist device 1 of the third embodiment is modified from the first embodiment in this regard, but provides similar action and effects as the first embodiment.

Fourth Embodiment

Figure 12:
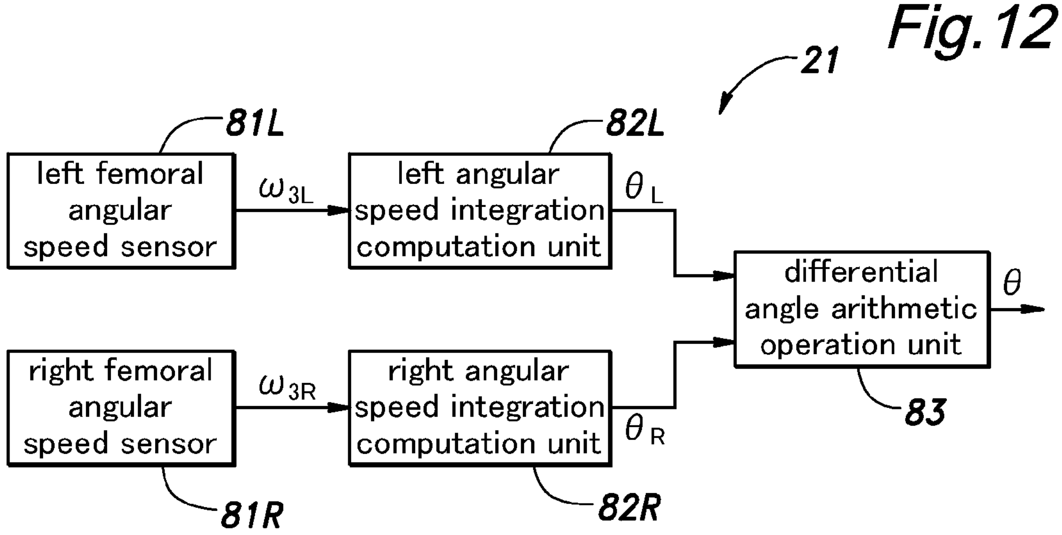
FIG. 12 is a block diagram of the differential angle computation unit of a fourth embodiment.

FIG. 12 shows the structure of the differential angle computation unit 21 in a fourth embodiment of the present invention.

In this embodiment, the walking assist device 1 is provided with a left femoral angular speed sensor 81L and a right femoral angular speed sensor 81R for detecting the angular speeds ω3L and ω3R of the respective femoral support units 3L and 3R, instead of the hip joint angular position sensors 6L and 6R of the first embodiment. The differential angle computation unit 21 computes the differential angle θ from the output signals provided by these femoral angular speed sensors 81L and 81R. The femoral angular speed sensors 81L and 81R may consist of gyro sensors, for instance.

The differential angle computation unit 21 is provided with a left and a right angular speed integration computation unit 82L and 82R for computing the hip joint angles of the respective femoral parts or the hip joint angles θL and θR by integrating the angular speeds ω3L and ω3R provided by the respective femoral angular speed sensors 81L and 81R, and a differential angle arithmetic operation unit 83 for computing the differential angle θ between the two femoral parts of the user P from the hip joint angles θL and θR computed by the respective angular speed integration computation unit 82L and 82R. The differential angle arithmetic operation unit 83 computes the differential angle θ by executing Equation (1) given above similarly as the first embodiment. The walking assist device 1 of the fourth embodiment is modified from the first embodiment in this regard, but provides similar action and effects as the first embodiment. In this case, in order for the values computed by each angular speed integration computation unit 82 not to diverge during computation, a low cut filter may be applied to the detection signals of the left and right angular speeds ωL and ωR.

Fifth Embodiment

Figure 13:
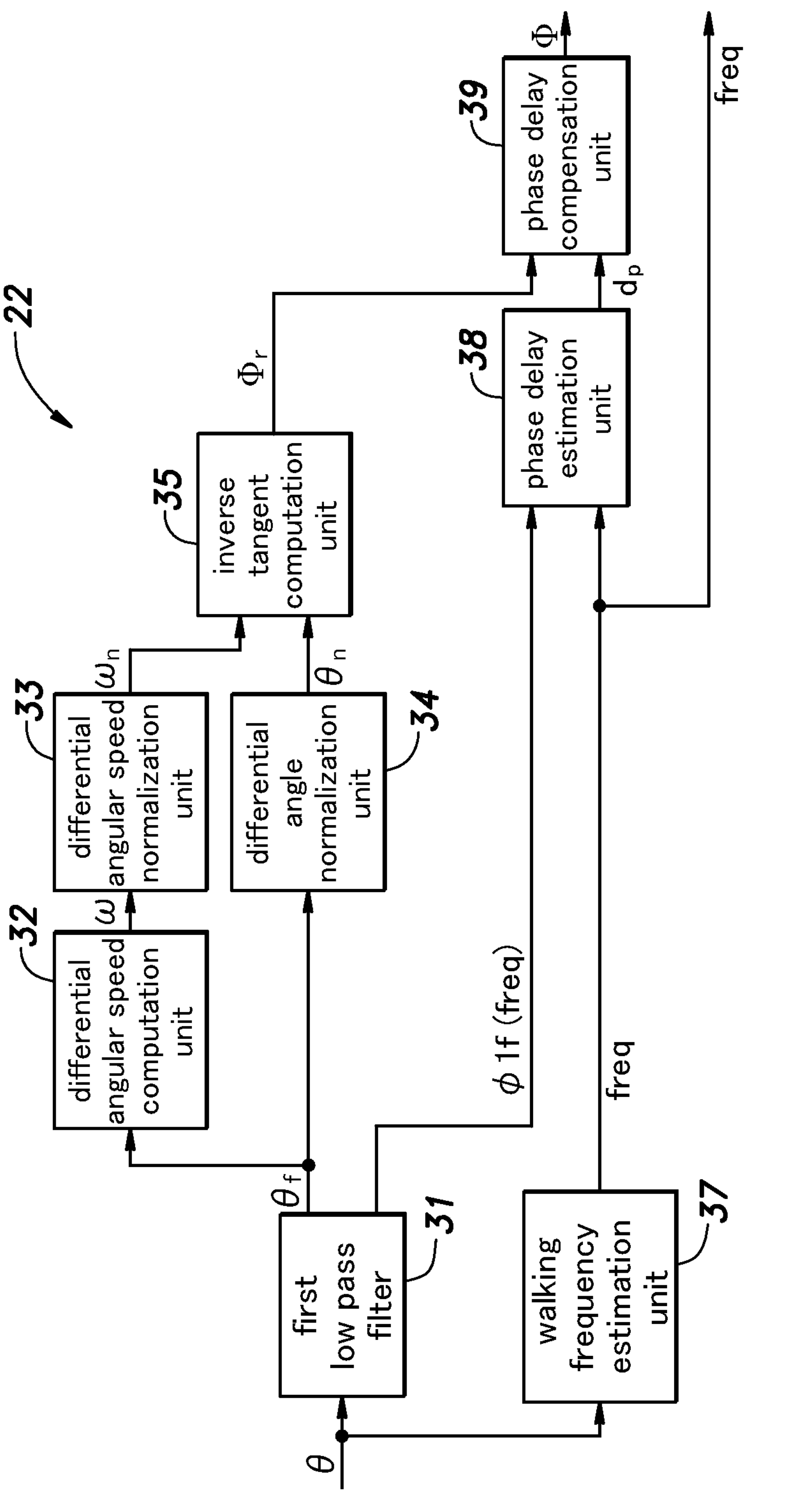
FIG. 13 is a block diagram of the differential angle phase computation unit of a fifth embodiment.

FIG. 13 shows a differential angle phase computation unit 22 of the fifth embodiment of the present invention which is modified from the differential angle phase computation unit 22 of the first embodiment shown in FIG. 3. In the description of the fifth to seventh embodiment, the parts of the differential angle phase computation unit 22 corresponding to those of the differential angle phase computation unit 22 of the first embodiment shown in FIG. 4 are denoted with like numerals, and only the parts which are different from those of the first embodiment are discussed in any detail in the following description.

In this embodiment, the second low pass filter 36 shown in FIG. 4 is omitted. Therefore, the phase delay estimation unit 38 estimates the phase delay dp by Equation (16) given in the following according to the phase property $\phi 1f$(freq) of the differential angle θ that has passed the first low pass filter 31 and the walking frequency freq computed by the walking frequency estimation unit 37.

$$dp=\phi 1f(\text{freq}) \qquad (16)$$

The differential angle phase computation unit 22 is thus modified from that of the first embodiment, but can provide the same action and effects as that of the first embodiment as long as the high frequency components of the differential angle θ is not particularly significant.

Sixth Embodiment

Figure 14:
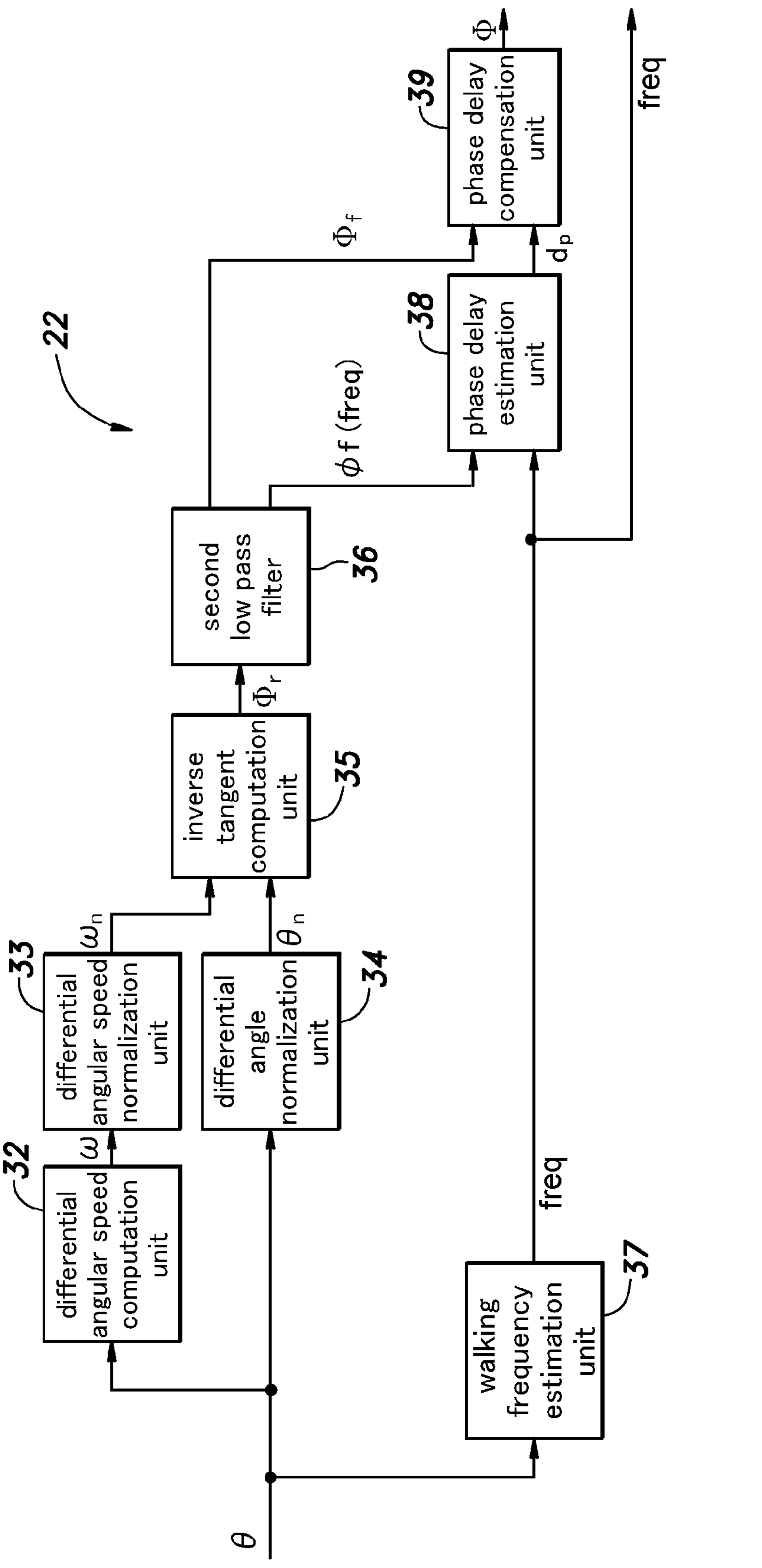
FIG. 14 is a block diagram of the differential angle phase computation unit of a sixth embodiment.

FIG. 14 shows a differential angle phase computation unit 22 of the sixth embodiment of the present invention. In this embodiment, the first low pass filter 31 shown in FIG. 4 is omitted. Therefore, the phase delay estimation unit 38 estimates the phase delay dp by Equation (17) given in the following according to the phase property $\phi 2f$(freq) of the differential angle phase Φ that has passed the second low pass filter 36 and the walking frequency freq computed by the walking frequency estimation unit 37.

$$dp=\phi 2f(\text{freq}) \qquad (17)$$

The differential angle phase computation unit 22 is thus modified from that of the first embodiment, but can provide the same action and effects as that of the first embodiment as long as the high frequency components of the differential angle θ are not particularly significant.

Seventh Embodiment

Figure 15:
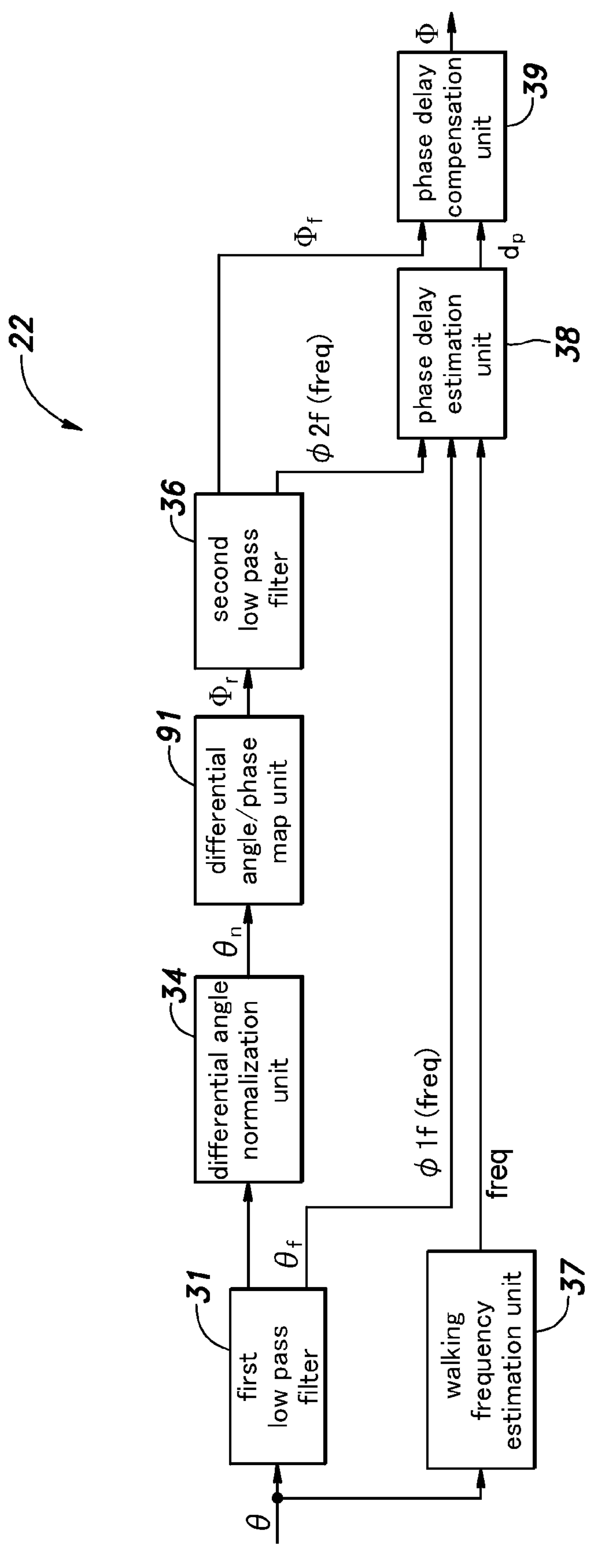
FIG. 15 is a block diagram of the differential angle phase computation unit of a seventh embodiment.

FIG. 15 shows the structure of the differential angle phase computation unit 22 of the seventh embodiment.

In this embodiment, the differential angular speed computation unit 32 and the differential angular speed normalization unit 33 shown in FIG. 4 are omitted, and a differential angle vs phase map unit 91 is provided instead of the inverse tangent computation unit 35. The differential angle vs phase map unit 91 is provided with a map defining the relationship between the normalized differential angle θn and the corresponding differential angle phase Φr based on measured data so that the differential angle phase Φr may be determined from the normalized differential angle θn by looking up this map.

The differential angle phase computation unit 22 is thus modified from that of the first embodiment, but can provide the same action and effects as that of the first embodiment.

Eighth Embodiment

Figure 16:
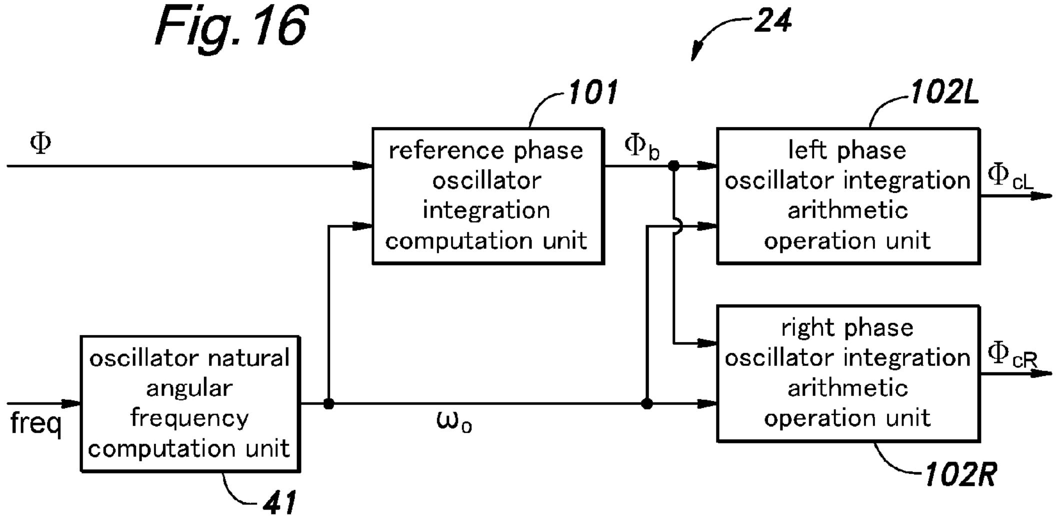
FIG. 16 is a block diagram of the differential angle phase computation unit of an eighth embodiment.
Figure 17:
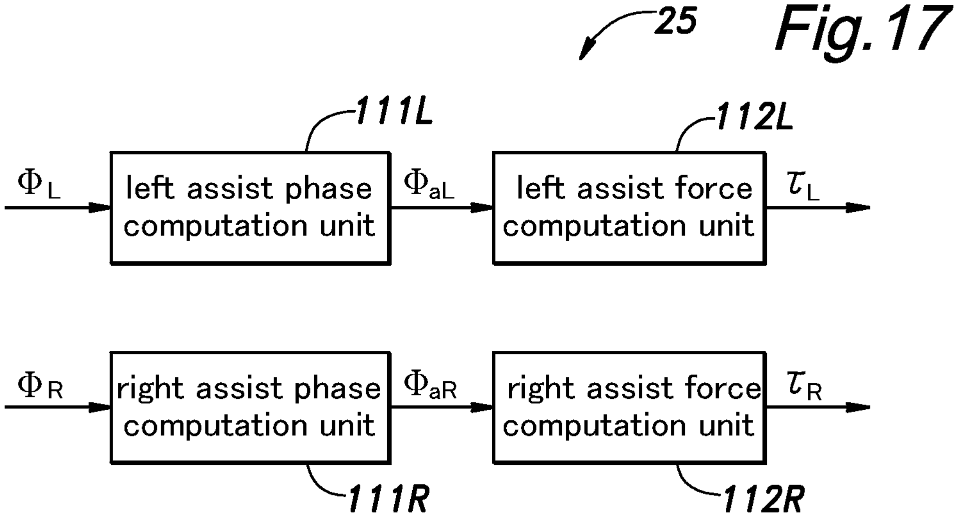
FIG. 17 is a block diagram of the assist force determination unit of the eighth embodiment.

FIGS. 16 and 17 show a modification of the assist force computation unit 23 (the oscillator phase computation unit 24 and the assist force determination unit 25) of the first embodiment shown in FIG. 3.

Figure 7:
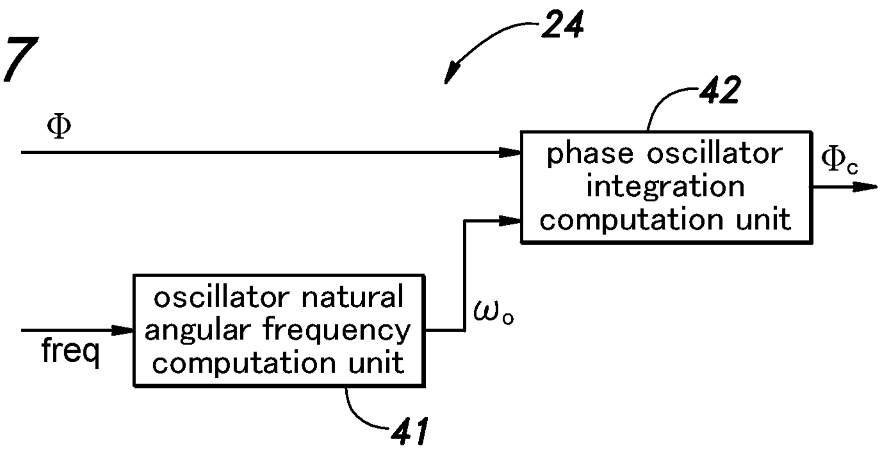
FIG. 7 is a block diagram of the oscillator phase computation unit shown in FIG. 3.

As shown in FIG. 16, the oscillator phase computation unit 24 of the eighth embodiment includes the oscillator natural angular frequency computation unit 41 similarly to that shown in FIG. 7, and a reference phase oscillator integration computation unit 101 and a left and a right phase oscillator integration arithmetic operation unit 102L and 102R, instead of the phase oscillator integration computation unit 42 shown in FIG. 7.

The reference phase oscillator integration computation unit 101 computes the oscillator phase Φb which oscillates in synchronism with the differential angle phase Φ according to the oscillator natural angular frequency ω0 computed by the oscillator natural angular frequency computation unit 41 by using the differential angle phase Φ corrected by the phase delay compensation unit 39 (FIG. 4) as an input, and produces the computed oscillator phase Φb of the differential angle. More specifically, the reference phase oscillator integration computation unit 101 computes the oscillator phase Φb that oscillate in synchronism with the differential angle phase Φ by executing an integration computation for solving a differential equation represented by Equation (18) given in the following.

$$d\Phi b/dt=\omega 0+f(\Phi-\Phi b+\alpha b) \qquad (18)$$

where f(x) represents a mathematical function, and αb denotes a preset phase difference for adjusting the reference oscillator phase Φb. Preferably, f(x) is a monotonously increasing function when x is near zero (when $-\pi/4<x<\pi/4$, for instance). For instance, f(x) may be represented by Equation (19) given in the following.

$$f(x)=Kb\sin(x) \qquad (19)$$

where Kb is a constant.

The left and right phase oscillator integration arithmetic operation units 102L and 102R compute the oscillator phases ΦcL and ΦcR of the left and right oscillators, respectively, that oscillate in synchronism with the reference oscillator phase Φb according to the oscillator natural angular frequency ω0 computed by the oscillator natural angular frequency computation unit 41 by using the differential angle phase Φb computed by the oscillator natural angular frequency computation unit 41 as an input, and produce the computed oscillator phases ΦcL and ΦcR of the left and right oscillators, respectively. As the computation is the same for the right and left oscillator phases, only the process executed by the left phase oscillator integration arithmetic operation unit 102L is described in the following. The left phase oscillator integration arithmetic operation unit 102L computes the left oscillator phase ΦcL that oscillates in synchronism with the reference oscillator phase Φb by executing an integration computation for solving a differential equation represented by Equation (20) given in the following.

$$d\Phi cL/dt=\omega 0+f(\Phi b-\Phi cL+\alpha L) \quad (20)$$

where f(x) represents a mathematical function, and αL denotes a preset phase difference for adjusting the left oscillator phase DCL. Preferably, f(x) is a monotonously increasing function when x is near zero (when $-\pi/4<x<\pi/4$, for instance). For instance, f(x) may be represented by Equation (21) given in the following.

$$f(x)=KL\sin(x) \quad (21)$$

where KL is a constant.

Of the preset phase difference αL in Equation (20) and the preset phase difference αb in Equation (18), only one of the may be used.

As shown in FIG. 17, the assist force determination unit 25 includes a left and a right assist phase computation unit 111L and 111R, and a left and a right assist force computation unit 112L and 112R. The left and right assist phase computation units 111L and 111R adjust the respective oscillator phases ΦcL and ΦcR computed by the left and right phase oscillator integration arithmetic operation units 102L and 102R (FIG. 16), respectively, so as to be the left and right assist force phases ΦasL and ΦasR that produce the assist force τ with an appropriate timing. More specifically, the left assist phase computation units 111L computes the left assist force phase ΦasL by executing Equation (22) given in the following, and the right assist phase computation units 111R computes the right assist force phase ΦasR by executing Equation (23) given in the following.

$$\Phi asL=\Phi L-\beta L \quad (22)$$

$$\Phi asR=\Phi R-\beta R \quad (23)$$

where βL is a left assist target phase difference, and βR is a right assist target phase difference.

The left and right assist force computation units 112L and 112R compute the left and right assist forces τL and τR according to the respective assist force phases ΦL and ΦR of the differential angle θ. More specifically, the left assist force computation unit 112L computes the left assist force τL by executing the computation of Equation (24) given in the following, and the right assist force computation unit 112R computes the right assist force τR by executing the computation of Equation (25) given in the following.

$$\tau L=G\times\sin\Phi asL \quad (24)$$

$$\tau R=G\times\sin\Phi asR \quad (25)$$

Alternatively, the left and right assist force computation units 112L and 112R may produce the left and right assist forces τL and τR by looking up maps (or tables) that define the relationship between the left assist force phase ΦasL and the left assist force τL and the relationship between the right assist force phase ΦasR and the right assist force τR, respectively.

The assist force computation unit 23 is thus modified from that of the first embodiment, but can provide the same action and effects as that of the first embodiment. In this embodiment, as the left and right assist forces τL and τR are computed individually, the walking motion of the user P can be assisted in a more smooth manner by providing a certain difference between the left and right assist forces τL and τR depending on the condition of the left and right legs of the user P wearing the walking assist device 1.

The present invention has been described in terms of specific embodiments, but is not limited by such embodiments, and can be modified and substituted without departing from the spirit of the present invention. For instance, in the foregoing embodiments, the differential angle phase Φ was modified by using a phase oscillator so that a non-cyclic walking pattern may be corrected to a more cyclic walking pattern. However, it is also possible to arrange such that the assist force computation unit 23 does not include the oscillator phase computation unit 24, and the assist force τ is computed from the differential angle phase Φ which the differential angle phase computation unit 22 in the assist force determination unit 25 has computed. Also, the algorithms and the equations used in the various embodiments are only exemplary, and are not limited to those explicitly mentioned in this disclosure.

GLOSSARY OF TERMS

1 walking assist device
2 main frame
3 (3L, 3R) femoral support unit (power transmission member, sub frame)
4 (4L, 4R) power unit
5 control unit
6 (6L, 6R) angular position sensor
21 differential angle computation unit
22 differential angle phase computation unit
23 assist force computation unit
24 oscillator phase computation unit
25 assist force determination unit
31 first low pass filter
32 differential angular speed computation unit
33 differential angular speed normalization unit
34 differential angle normalization unit
35 inverse tangent computation unit
36 second low pass filter
37 walking frequency estimation unit
38 phase delay estimation unit
39 phase delay compensation unit
41 oscillator natural angular frequency computation unit
42 phase oscillator integration computation unit
51 assist phase computation unit
52 right and left assist force computation unit
91 differential angle/phase map unit
111L left assist phase computation unit
111R right assist phase computation unit
112L left assist force computation unit
112L right assist force computation unit
P user (wearer)
dp phase delay
freq walking frequency
Φ differential angle phase
Φc oscillator phase
Φas assist force phase
ΦasL left assist force phase
ΦasR right assist force phase
θL hip joint angle of left femoral part
θR hip joint angle of right femoral part
θ differential angle
θn normalized differential angle
τ assist force (assist torque)
τL left assist force
τR right assist force
ω differential angular speed
ωn normalized differential angular speed
ω0 oscillator natural angular frequency

The invention claimed is:

1. A walking assist device including a main frame configured to be worn by a user, a power unit mounted on the main frame, a pair of power transmission members pivotally attached to the main frame so as to be rotatable about respective hip joints of the user and to transmit assist force provided by the power unit to left and right femoral parts of the user and a control unit for controlling an operation of the power unit, wherein the control unit comprises:

a differential angle computation unit for computing a differential angle between an angular position of the left femoral part of the user relative to a coronal plane of the user and an angular position of the right femoral part of the user relative to the coronal plane of the user;

a differential angle phase computation unit for computing a differential angle phase according to the differential angle; and an assist force computation unit for computing an assist force to be applied to the user according to the differential angle phase.

2. The walking assist device according to claim 1, wherein the differential angle phase computation unit comprises:

a differential angular speed computation unit for computing a differential angular speed according to the differential angle;

a differential angular speed normalization unit for normalizing the differential angular speed;

a differential angle normalization unit for normalizing the differential angle; and an inverse tangent computation unit for computing the differential angle phase by performing an inverse tangent computation on the differential angle normalized by the differential angle normalization unit and the differential angular speed normalized by the differential angular speed normalization unit.

3. The walking assist device according to claim 1, wherein the differential angle phase computation unit comprises:

a differential angle normalization unit for normalizing the differential angle; and a map unit for determining the differential angle phase according to the normalized differential angle by using a map defining a relationship between the differential angle phase and the normalized differential angle.

4. The walking assist device according to claim 1, wherein the differential angle phase computation unit comprises:

a filter unit for filtering at least one of the differential angle and the differential angle phase;

a walking frequency estimation unit for estimating a walking frequency according to the differential angle;

a phase delay estimation unit for estimating a phase delay caused by the filter unit according to the walking frequency; and a phase delay compensation unit for compensating the phase delay of the differential angle phase according to the estimated phase delay.

5. The walking assist device according to claim 1, wherein the assist force computation unit comprises:

an oscillator phase arithmetic operation unit for computing a phase of an oscillator that oscillates in synchronism with the differential angle phase; and an assist force determination unit for determining the assist force according to the oscillator phase computed by the oscillator phase computation unit.

6. The walking assist device according to claim 5, wherein the oscillator phase computation unit comprises:

an oscillator natural angular frequency computation unit for computing a natural angular frequency of a phase oscillator corresponding to the walking frequency of the user determined from the differential angle; and a phase oscillator integration computation unit for computing the oscillator phase by performing an integration computation on a phase change of the phase oscillator by taking into account a phase difference between the differential angle phase and the oscillator phase.

7. The walking assist device according to claim 6, wherein the oscillator natural angular frequency computation unit is configured to compute the natural angular frequency of the phase oscillator by using the walking frequency determined from the differential angle.

8. The walking assist device according to claim 1, wherein the assist force determination unit comprises:

an assist phase computation unit for computing, from the differential angle phase, an assist force phase adjusted to cause the assist force to be produced at an appropriate timing; and a right and a left assist force computation unit for computing assist forces for the left and right femoral parts of the user according to the assist force phase.

9. The walking assist device according to claim 8, wherein the assist force determination unit comprises:

a left assist phase computation unit for adjusting the differential angle phase so as to be a left assist force phase that allows the assist force for the left femoral part to be produced at an appropriate timing;

a left assist force computation unit for computing the left assist force according to the left assist force phase;

a right assist phase computation unit for adjusting the differential angle phase so as to be a right assist force phase that allows the assist force for the right femoral part to be produced at an appropriate timing; and a right assist force computation unit for computing the right assist force according to the right assist force phase.

* * * * *